(12) United States Patent
Mujwid et al.

(10) Patent No.: US 11,324,595 B2
(45) Date of Patent: May 10, 2022

(54) INFLATABLE PENILE PROSTHESIS WITH A STRUCTURED CYLINDER

(71) Applicant: Boston Scientific Scimed, Inc., Maple Grove, MN (US)

(72) Inventors: James Ryan Mujwid, Hudson, WI (US); Jessica Elizabeth Felton, Minneapolis, MN (US); Ryan Earl Fredrick, Eden Prairie, MN (US); John Anders Bostrom, Saint Paul, MN (US); Thomas Andrew Albrecht, Edina, MN (US); Mark Edward DiLoreto, Chaska, MN (US); Mitul Shah, Hopkins, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 84 days.

(21) Appl. No.: 16/262,016

(22) Filed: Jan. 30, 2019

(65) Prior Publication Data
US 2019/0240026 A1  Aug. 8, 2019

Related U.S. Application Data

(60) Provisional application No. 62/626,894, filed on Feb. 6, 2018.

(51) Int. Cl.
*A61F 2/26* (2006.01)

(52) U.S. Cl.
CPC .......... *A61F 2/26* (2013.01); *A61F 2240/004* (2013.01); *A61F 2250/0003* (2013.01); *A61F 2250/0013* (2013.01); *A61F 2250/0035* (2013.01)

(58) Field of Classification Search
CPC ........................................................ A61F 2/26
USPC ...................................................... 600/38–40
See application file for complete search history.

(56) References Cited

U.S. PATENT DOCUMENTS

| 4,881,530 | A | 11/1989 | Trick et al. |
| 5,067,485 | A | 11/1991 | Cowen et al. |
| 5,167,611 | A | 12/1992 | Cowan |
| 6,558,315 | B1 * | 5/2003 | Kuyava .............. A61F 2/26 600/40 |
| 2009/0105530 | A1 | 4/2009 | Kuyava et al. |
| 2009/0132043 | A1 | 5/2009 | George et al. |
| 2010/0036196 | A1 | 2/2010 | Walch et al. |

(Continued)

FOREIGN PATENT DOCUMENTS

WO  2014052729 A2  4/2014

OTHER PUBLICATIONS

International Search Report and Written Opinion for International Application No. PCT/US2019/015974, dated May 22, 2019, 16 pages.

(Continued)

*Primary Examiner* — John P Lacyk
(74) *Attorney, Agent, or Firm* — Brake Hughes Bellermann LLP

(57) ABSTRACT

According to an aspect, an implant includes an inflatable member and a pump assembly configured to facilitate a transfer of a fluid from the reservoir to the inflatable member. The inflatable member has a sidewall that defines a lumen. The sidewall has an outer surface and an inner surface disposed opposite the outer surface. The inner surface has a series of undulations.

20 Claims, 13 Drawing Sheets

(56) References Cited

U.S. PATENT DOCUMENTS

2015/0375419 A1 12/2015 Günther et al.
2016/0100945 A1 4/2016 Little et al.

OTHER PUBLICATIONS

First Examination Report for Australian Application No. 2019217338, dated Jul. 27, 2020, 5 pages.
Second Examination Report for Australian Application No. 2019217338, dated Jun. 29, 2021, 5 pages.
Third Examination Report for Australian Application No. 2019217338, dated Jul. 8, 2021, 3 pages.

* cited by examiner

INFLATABLE PENILE PROSTHESIS WITH A STRUCTURED CYLINDER

CROSS-REFERENCE TO RELATED APPLICATION

This application is a Nonprovisional of, and claims priority to, U.S. Patent Application No. 62/626,894, filed on Feb. 6, 2018, entitled "INFLATABLE PENILE PROSTHESIS WITH A STRUCTURED CYLINDER", which is incorporated by reference herein in its entirety

TECHNICAL FIELD

This disclosure relates generally to bodily implants and more specifically to bodily implants, such as penile prostheses that include inflatable members.

BACKGROUND

One treatment for male erectile dysfunction is the implantation of a penile prosthesis that mechanically erects the penis. Some existing penile prostheses include inflatable cylinders or members that can be inflated or deflated using a pump mechanism. In some existing devices, the inflatable cylinder or member requires a relatively large amount of force to inflate. Additionally, in some existing devices, the pump mechanism may require many sequential squeezes or activations to inflate the cylinder or member. Furthermore, in some existing devices, the inflatable cylinder or member may assume a flat, unnatural shape when in a deflated configuration.

Accordingly, it would be useful to provide a bodily implant, such as a penile prosthesis, that includes an improved cylinder or member that can be more easily inflated. Additionally, it would be useful to provide a bodily implant, such as a penile prosthesis, that includes an inflatable cylinder or member that may assume a natural shape when in the deflated configuration.

SUMMARY

According to an aspect, an implant includes an inflatable member and a pump assembly configured to facilitate a transfer of a fluid from the reservoir to the inflatable member. The inflatable member has a sidewall that defines a lumen. The sidewall has an outer surface and an inner surface disposed opposite the outer surface. The inner surface has a series of undulations.

In some embodiments, the inflatable member defines a longitudinal axis, the series of undulations extend along the longitudinal axis.

In some embodiments, the lumen defined by the sidewall of the inflatable member includes a first portion having a first diameter and second portion having a second diameter, the second diameter being larger than the first diameter. In some embodiments, the lumen defined by the sidewall of the inflatable member includes a first portion having a first diameter, a second portion having a second diameter, and a third portion having a third diameter, the second portion being disposed between the first portion and the third portion, the second diameter begin larger than the first diameter, the second diameter being larger than the third diameter. In some embodiments, the lumen defined by the sidewall of the inflatable member includes a first portion having a first diameter, a second portion having a second diameter, and a third portion having a third diameter, the second portion being disposed between the first portion and the third portion, the second diameter begin larger than the first diameter, the second diameter being larger than the third diameter, the second portion being disposed between the first portion and the third portion along a longitudinal axis of the inflatable member.

In some embodiments, the outer surface of the inflatable member is substantially smooth. In some embodiments, the outer surface of the inflatable member includes a series of undulations.

In some embodiments, the inflatable member is unitarily formed. In some embodiments, the inflatable member is monolithic.

In some embodiments, the inflatable member is configured to be placed in an inflated configuration and a deflated configuration. In some embodiments, the inflatable member is configured to be placed in an inflated configuration and a deflated configuration, the inflatable member having a tubular shape when in the deflated configuration. In some embodiments, the inflatable member is configured to be placed in an inflated configuration and a deflated configuration, the inflatable member configured to extend along a longitudinal axis of the inflatable member when placed in the inflated configuration.

In some embodiments, the implant includes a first cap coupled to a first end portion of the inflatable member; and a second cap coupled to a second end portion of the inflatable member.

In some embodiments, the implant includes a reservoir configured to retain the fluid, wherein the pump is configured to help facilitate a transfer of the fluid from the reservoir to the inflatable member when the implant is in an inflation mode.

In some embodiments, the pump assembly includes a valve body and a pump bulb member.

According to another aspect, an apparatus includes a core member. The core member has a longitudinal axis and an outer surface. The outer surface has a series of undulations. The core member is formed of a material that is configured to dissolve.

In some embodiments, the core member defines a lumen, the lumen extends substantially parallel to the longitudinal axis of the core member.

According to another aspect, a method of making an elongate member includes forming a core member; disposing the core member within a lumen of a casing; and removing the core member from the casing.

In some embodiments, the core member has a longitudinal axis and an outer surface, the outer surface has a series of undulations, the core member is formed of a material that is configured to dissolve. In some embodiments, the removing the core member from the casing includes dissolving the core member.

DETAILED DESCRIPTION

Figure 1:
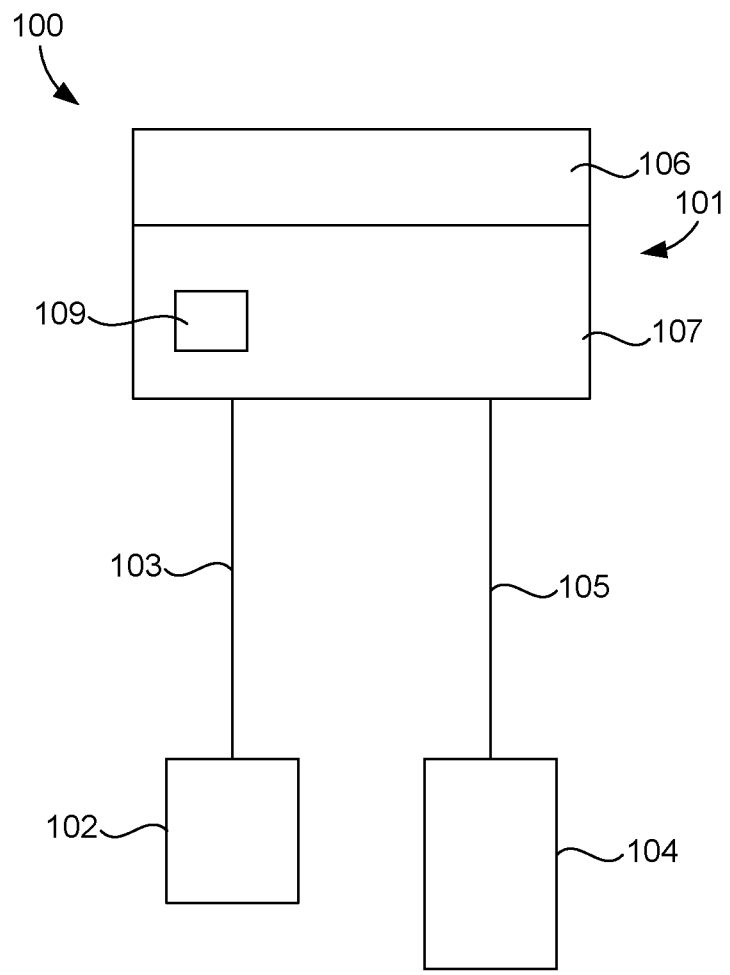
FIG. 1 schematically illustrates a penile prosthesis according to an embodiment.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices such as penile prostheses or other bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The terms proximal and distal described in relation to various devices, apparatuses, and components as discussed in the subsequent text of the present disclosure are referred with a point of reference. The point of reference, as used in this description, is a perspective of a person who implants the inflatable penile prosthesis. The person may be a surgeon, a physician, a nurse, a doctor, a technician, and the like who may perform the implantation procedure. The term proximal refers to an area or portion that is closer or closest to the person (the surgeon, physician, nurse, doctor, technician, or the like) during the implantation procedure. The term distal refers to an area or portion that is farther or farthest from the person (the surgeon, physician, nurse, doctor, technician, or the like).

The embodiments discussed herein may improve the performance of an inflatable member of the device. For example, the inflatable member may have improved stiffness or rigidity, improved reliability, or improved deflation or inflation times. In some embodiments, the inflatable member may be facilitated by requiring less force or pressure to inflate the inflatable member. Additionally, in some embodiments, the inflatable member may retain or maintain a tubular shape when the inflatable member is placed in its deflated configuration.

The embodiments may include an inflatable penile prosthesis having a pump assembly, an inflatable member, and a reservoir. The inflatable member may be implanted into the corpus cavernosae of a patient or user, the reservoir may be implanted in the user's abdomen, and the pump assembly may be implanted in the scrotum. The pump assembly may switch between an inflation position and a deflation position such that a user can operate the device to place the inflatable penile prosthesis in either an inflation mode to transfer fluid from the reservoir to the inflatable member or a deflation mode to transfer the fluid from the inflatable member back to the reservoir.

FIG. 1 schematically illustrates an inflatable penile prosthesis 100 according to an aspect. The inflatable penile prosthesis 100 may include a reservoir 102, a cylinder or inflatable member 104, and a pump assembly 101 configured to transfer fluid between the reservoir 102 and the inflatable member 104. In some examples, the inflatable member 104 may be implanted into the corpus cavernosae of the user, the reservoir 102 may be implanted in the abdomen or pelvic cavity of the user (e.g., the reservoir 102 may be implanted in the lower portion of the user's abdominal cavity or the upper portion of the user's pelvic cavity), and the pump assembly 101 may be implanted in the scrotum of the user.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. The volumetric capacity of the inflatable member 104 may depend on the size of the cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

In some embodiments, the inflatable member 104 is a structured member or includes structural elements. For example, in some embodiments, the inflatable member may include a sidewall that defines a lumen. The sidewall may include structural features (such as locations of increased or decreased thickness). In some embodiments, the structural features may allow the inflatable member to be inflated at a relatively low pressure. In some embodiments, this may allow the user to inflate the inflatable member 104 with less pumps or activations of the pump or may allow the user to apply less force to the pump to inflate the inflatable member 104. Details of the pump assembly 101 are described below. Additionally, in some embodiments, the structural features of the inflatable member 104 may allow the inflatable member 104 to retain or maintain a tubular shape (or a more anatomically correct shape) when the inflatable member 104 is in its deflated configuration.

The reservoir 102 may include a container having an internal chamber configured to hold or house fluid that is used to inflate the inflatable member 104. The volumetric capacity of the reservoir 102 may vary depending on the size of the inflatable penile prosthesis 100. In some examples, the volumetric capacity of the reservoir 102 may be 3 to 150 cubic centimeters. In some examples, the reservoir 102 is constructed from the same material as the inflatable member 104. In other examples, the reservoir 102 is constructed from a different material than the inflatable member 104.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 may be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 may include a single or multiple tube members for transferring the fluid between the pump assembly 101 and the inflatable member 104. In some examples, the first conduit connector 103 and the second conduit connector 105 may include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 includes a pump (also referred to as a pump bulb member) 106 and a valve body 107. The valve body 107 also includes a selection member 109. The selection member 109 may be used to select or change the mode in which the pump assembly is in. For example, the selection member 109 may be moved from a first position to a second position to place the device in its deflation mode. The selection member 109 may then be moved back to its first position to place the device in its inflation mode. In some embodiments, the selection member 109 is movable with respect to the valve body 107. For example, in some embodiments, the selection member 109 is slidably coupled or slideable with respect to the valve body 107.

The pump 106 may be squeezed or depressed by the user in order to facilitate the transfer of fluid from the reservoir 102 to the inflatable member 104. For example, in the inflation mode, while the user is operating the pump 106, the pump 106 may receive the fluid from the reservoir 102, and then output the fluid to the inflatable member 104. When the user switches to the deflation mode, at least some of the fluid can automatically be transferred back to the reservoir 102 (due to the difference in pressure from the inflatable member 104 to the reservoir 102). Then, the user may squeeze the inflatable member 104 to facilitate the further transfer of fluid through the pump 106 to the reservoir 102.

In some examples, the pump 106 may include a flexible member defining a cavity. In some examples, the pump 106 may define a pump shell having a flexible bulb and a valve body connector, where the valve body connector is designed to fit at least partially over the valve body 107. In some examples, the pump 106 may include a squeeze pump. In some examples, the pump 106 may include a portion that is round or substantially round. In some examples, the pump 106 may include ribbing or dimples to aid the user in gripping the pump 106. The pump 106 may use suction and pressure to move the fluid in and out of the cavity of the pump 106 in the inflation mode. For example, the user may depress or squeeze the pump 106 to expel the fluid out of the cavity, and, when the flexible member returns to its original shape, the resulting suction pushes the fluid into the cavity of the pump 106. In some examples, the pump 106 may have a bulb spring rate that is designed to refill the pump 106 in a selected time frame.

As discussed above, the selection member 109 may be used to select or change the mode in which the pump assembly is in. For example, in one embodiment, the selection member 109 may be placed in the inflate position and the user may then operate the pump 106 to inflate the inflatable member 104 (i.e., move the fluid from the reservoir 102 to the inflatable member 104). For example, the user may repeatedly depress or squeeze the pump 106 until the desired rigidity is achieved.

In some examples, if the reservoir 102 is at least partially pressurized, the fluid may automatically flow out of the reservoir 102 and into the inflatable member 104 without the user depressing or squeezing the pump 106 until the pressure is at least partially equalized between the reservoir 102 and the inflatable member 104.

Then, when the user wants to deflate the inflatable member 104, the user moves selection member 109 to its deflated position. The user may then operate the pump 106 to deflate the inflatable member 104 (i.e., move the fluid from the inflatable member 104 to the reservoir 102). The pump 106 may then return to its original form, which provides a suction force causing fluid to be drawn into the pump 106 from the inflation member 104. The fluid from the inflation member 104 fills the pump 106 (or at least partially fills the pump 106). This pump cycle is repeated until the inflatable member 104 is deflated.

In some examples, the fluid may automatically (upon movement of the selection member 109 to its deflate position) flow out of the inflatable member 104 and into the reservoir 102 without the user depressing or squeezing the pump 106 until the pressure is at least partially equalized between the reservoir 102 and the inflatable member 104.

In some examples, after the inflation member 104 has been deflated, the pump 106 may be squeezed to place the pump in a contracted position or configuration.

Figure 2:
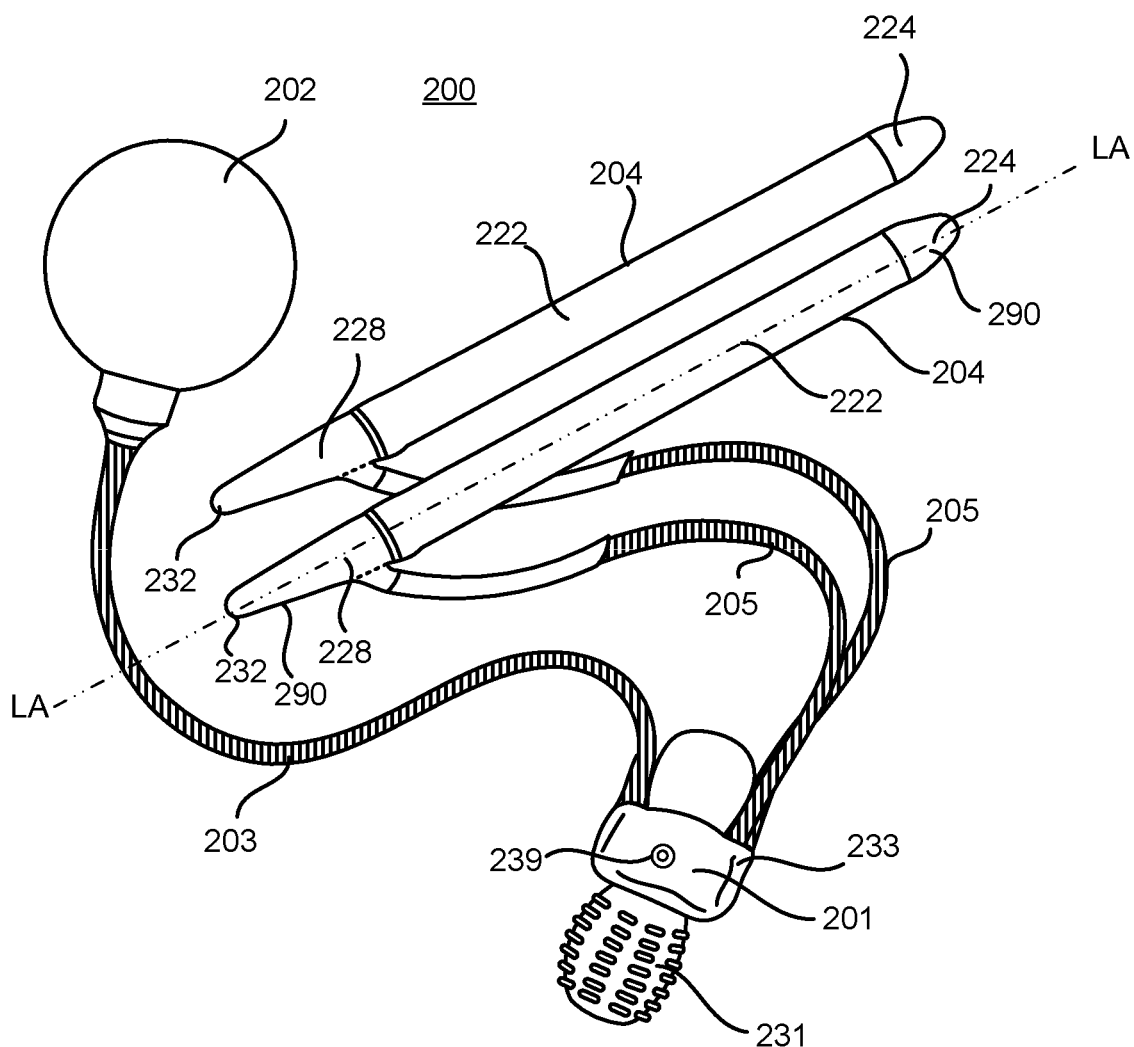
FIG. 2 illustrates a penile prosthesis according to another embodiment.
Figure 3:
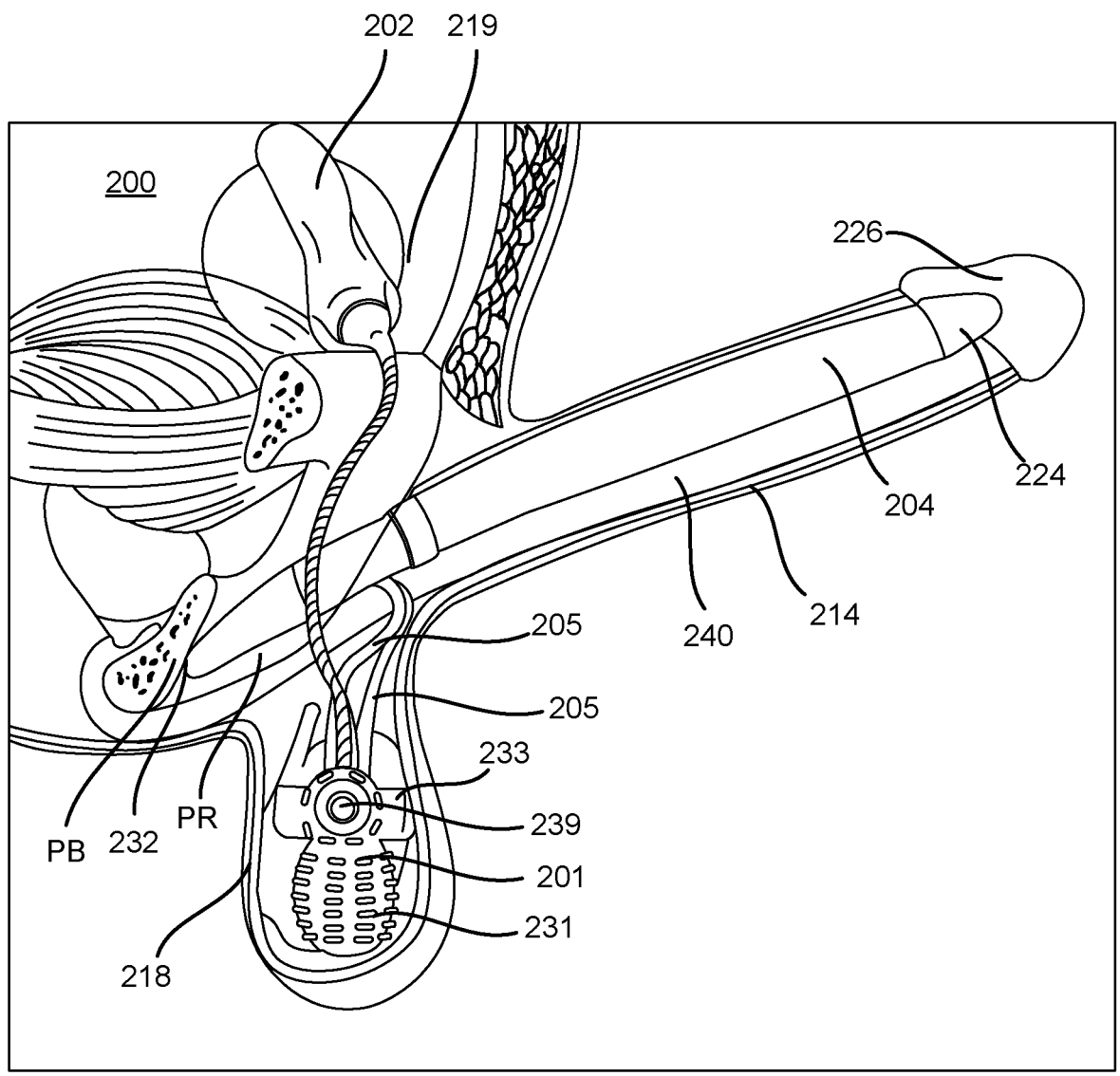
FIG. 3 illustrates the penile prosthesis of FIG. 2 implanted within a patient according to an embodiment.

FIG. 2 illustrates a penile prosthesis 200 according to an aspect. FIG. 3 schematically illustrates the penile prosthesis 200 placed within a body of the user or patient.

The penile prosthesis 200 may include a pair of cylinders 204, and the pair of cylinders or inflatable members 204 are implanted in a penis 214. For example, one of the cylinders 204 may be disposed on one side of the penis 214. The other cylinder 204 (not shown in FIG. 3) of the pair of cylinders may be disposed on the other side of the penis 214. The cylinder 204 may include a distal end portion 224, a cavity or inflation chamber 222, and a proximal end portion 228 having a rear tip 232.

The penile prosthesis 200 may include a pump assembly 201, which may be implanted into the patient's scrotum 218. A pair of conduit connectors 205 may attach the pump assembly 201 to the pair of inflatable members or cylinders 204 such that the pump assembly 201 is in fluid communication with the pair of inflatable members or cylinders 204. Also, the pump assembly 201 may be in fluid communication with a reservoir 202 via a conduit connector 203. The reservoir 202 may be implanted into the user's abdomen 219. The inflation chamber or portion 222 of the cylinder 204 may be disposed within the penis 214. The distal end portion 224 of the cylinder 204 may be at least partially disposed within the crown portion 226 of the penis 214. The proximal end portion 228 may be implanted into the patient's pubic region PR with the rear tip 232 proximate the pubic bone PB.

In order to implant the inflatable members or cylinders 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of inflatable members or cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area (proximal corpora cavernosae) to prepare the patient to receive the proximal end portion 228. The surgeon may measure the length of the proximal and distal corpora cavernosae from the incision and the dilated region of the pubic area to determine an appropriate size of the inflatable members or cylinders 204 to implant.

After the patient is prepared, the penile prosthesis 200 is implanted into the patient. The distal tip of the distal end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown of the penis 214. The surgeon tugs on the suture to pull the cylinder 204 into the corpus cavernosum. This is done for each cylinder of the pair of cylinders 204. Once the inflation chamber 222 is in place, the surgeon may remove the suture from the distal tip. The surgeon then inserts the proximal end portion 228. The surgeon inserts the rear end of the cylinder 204 into the incision and forces the proximal end portion 228 toward the pubic bone PB until each cylinder 204 is in place.

Figure 4A:
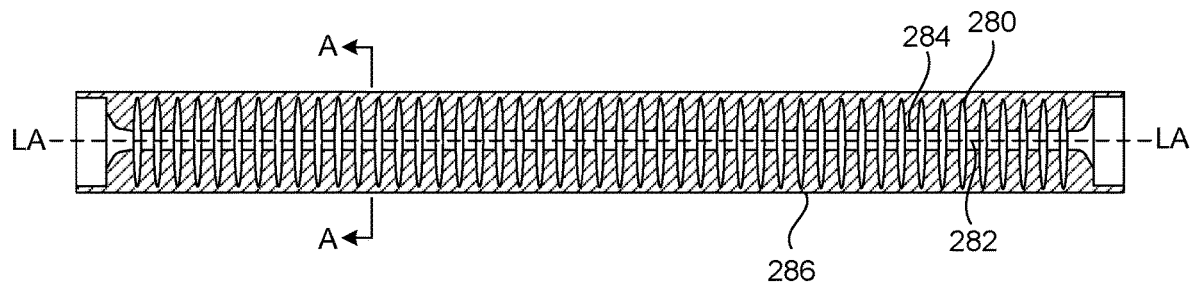
FIGS. 4A, 4B, and 4C are cross-sectional views of an inflatable member according to an embodiment.
Figure 4B:
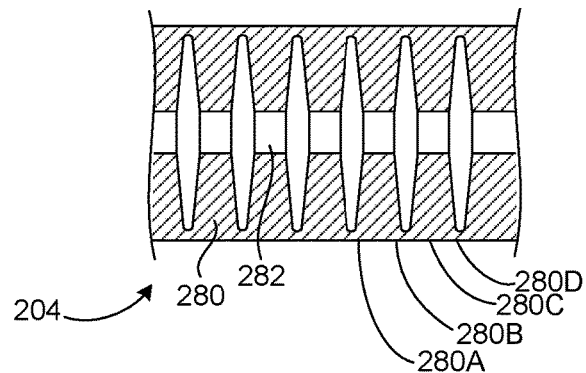
Figure 4C:
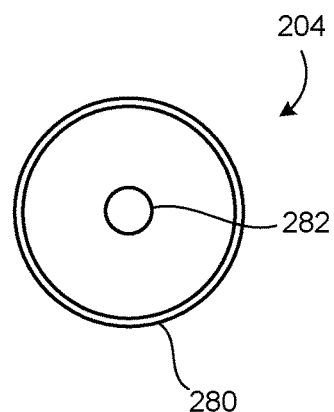

In the illustrated embodiment, each of the inflatable members or cylinders 204 is structurally and functionally similar. Accordingly, only one of the inflatable members or cylinders will be discussed in detail. FIG. 4A is a cross-sectional view of the inflatable member 404 taken along the longitudinal axis LA of the inflatable member 404. FIG. 4B is a cross-sectional view of a portion of the inflatable member 404. FIG. 4C is a cross-sectional view of the inflatable member 404 taken along line A-A of FIG. 4A. The inflatable member 204 may be capable of expanding upon the injection of fluid into a cavity of the inflatable member 204. For instance, upon injection of the fluid into the inflatable member 204, the inflatable member 204 may increase its length and/or width, as well as increase its rigidity. The volumetric capacity of the inflatable member 204 may depend on the size of the cylinders. In some examples, the volume of fluid in each cylinder may vary from about 10 milliliters in smaller cylinders and to about 50 milliliters in larger sizes.

In the illustrated embodiment, the inflatable member 204 includes a sidewall 280 that defines a lumen or cavity 282. In the illustrated embodiment, the inflatable member 204 includes structural features. In some embodiments, the structural features may allow the inflatable member to be inflated at a relatively low pressure. In some embodiments, this may allow the user to inflate the inflatable member 204 with less pumps or activations of the pump or may allow the user to apply less force to the pump to inflate the inflatable member 204. Additionally, in some embodiments, the structural features of the inflatable member 204 may allow the inflatable member 204 to retain or maintain a tubular shape (or a more anatomically correct shape) when the inflatable member 204 is in its deflated configuration.

In the illustrated embodiment, the structural features of the inflatable member 204 include a sidewall 280 that includes structural features. The sidewall 280 has an inner surface 284 and an outer surface 286. The outer surface 286 is disposed opposite the inner surface 284. The inner surface 284 defines the cavity or lumen 282 (and is disposed adjacent the lumen 282). The inner surface 284 of the sidewall 280 has a series of undulations. In other words, the inner surface 284 of the sidewall 280 is not smooth. The series of undulations extend along the longitudinal axis LA of the inflatable member 204. In the illustrated embodiment, the outer surface 286 is smooth (or devoid of undulations). In other embodiments, the outer surface includes a series of undulations and is not smooth.

In the illustrated embodiment, the sidewall 280 includes portions of increased thickness and portions of decreased thickness. For example, at location 280A the sidewall 280 has a smaller or decreased thickness. At location 280B, the sidewall 280 has a larger or increased thickness. The thickness of the sidewall 280 at location 280A is smaller than at location 280B. The sidewall 280 has a smaller or decreased thickness at location 280C. The sidewall 280 has a larger or increased thickness at location 280D. Locations 280A, 280B, 280C, and 280D are disposed along the longitudinal axis LA of the inflatable member 204 with location 280B being disposed between 280A and 280C and location 280C being disposed between 280B and 280D.

In the illustrated embodiment, the size or diameter of the lumen 282 defined by the sidewall 280 varies along the longitudinal axis LA of the inflatable member. Specifically, as illustrated, the portion of the lumen disposed adjacent location 280A of the sidewall 280 is larger than the portion of the lumen disposed adjacent location 280B of the sidewall 280. Similarly, the portion of the lumen disposed adjacent location 280C of the sidewall 280 is larger than the portion of the lumen disposed adjacent location 280D of the sidewall 280.

Figure 10:
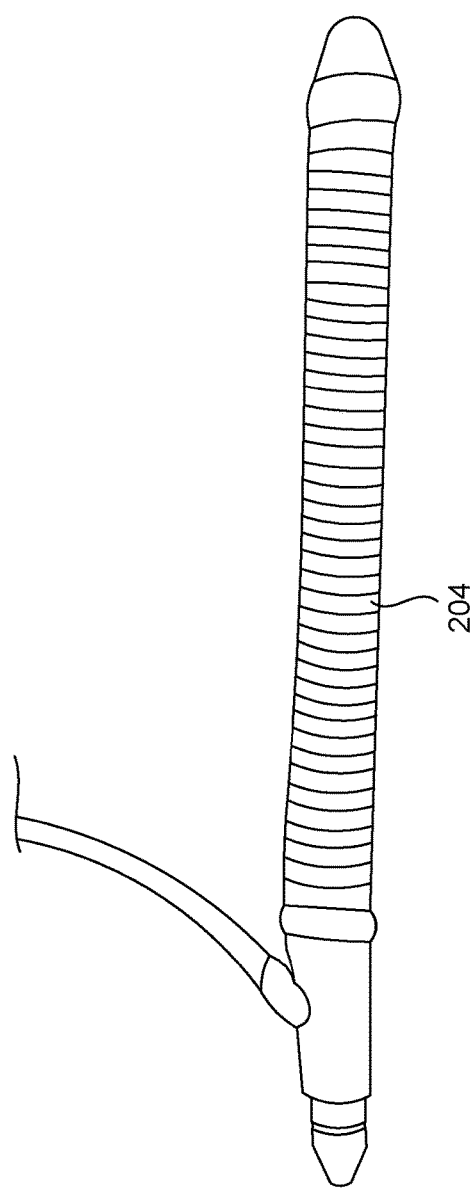
FIGS. 10-11 are side views of an inflatable member according to an embodiment.
Figure 11:
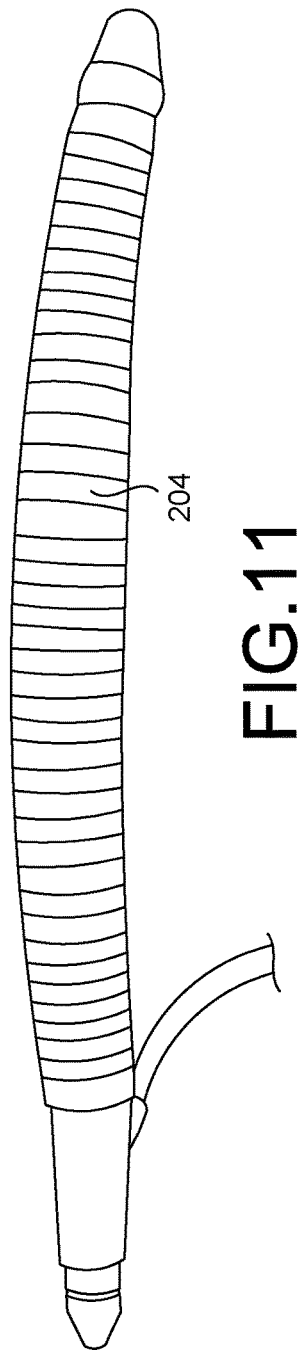

As best illustrated FIGS. 10 and 11, the inflatable member 204 is configured to expand along the longitudinal axis (increase in length) and expand radially when the inflatable member 204 is place in its inflated configuration. FIG. 10 is a side view of the inflatable member 204 in its deflated configuration. FIG. 11 is a side view of the inflatable member 204 in its inflated configuration. As illustrated, inflatable member 204 is longer in length and is larger in radial size in its inflated configuration.

Figure 12:
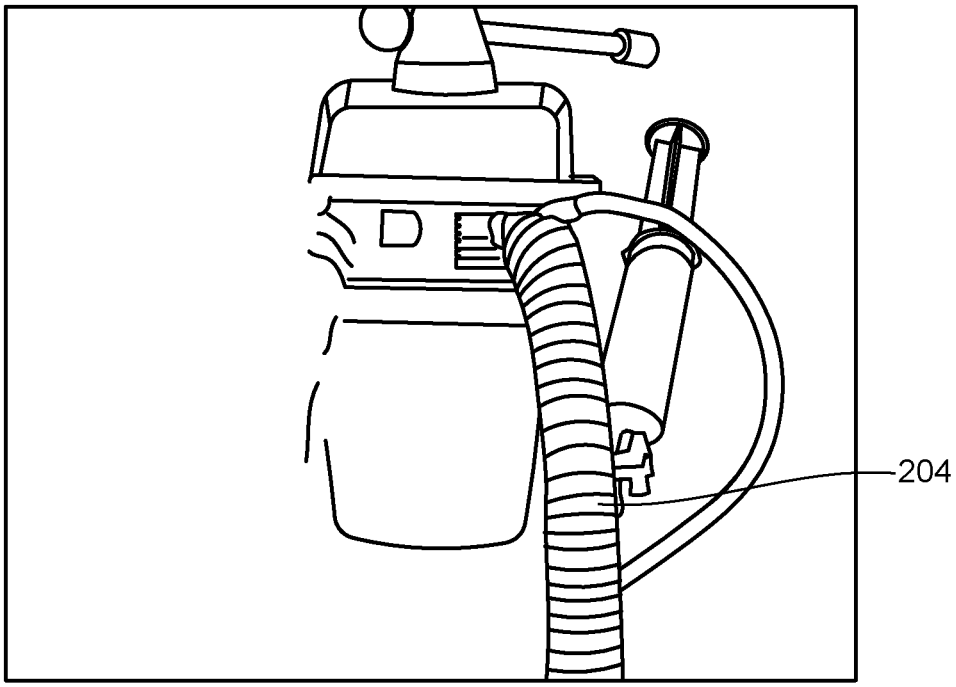
FIG. 12 is a front view of an inflatable member according to an embodiment.
Figure 13:
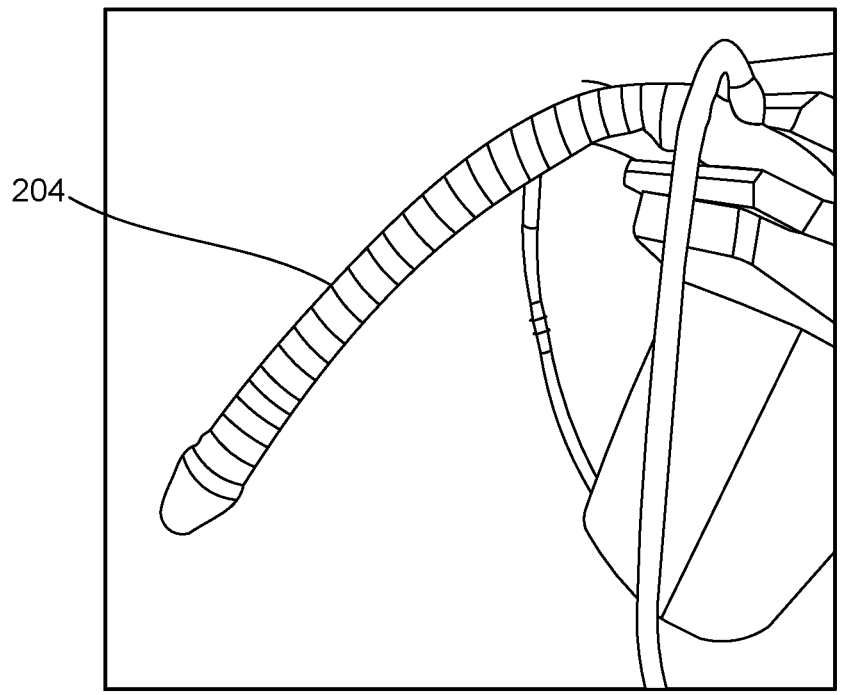
FIG. 13 is a side view of the inflatable member of FIG. 12.

FIG. 12 is a front view of the inflatable member 204 in its deflated or relaxed configuration. FIG. 13 is a side view of the inflatable member in its relaxed configuration. As best illustrated in FIGS. 12 and 13, the inflatable member 204 is configured to retain or maintain a tubular shape when the inflatable member 204 is disposed in its deflated or relaxed configuration. In some embodiments, by retaining a tubular or substantially tubular shape, the inflatable member 204 does not flatten or fold when the inflatable member 204 is disposed in its deflated or relaxed configuration. In some embodiments, this allows the inflatable member to more correctly assume a natural bodily shape (such as a flaccid penis).

Figure 8:
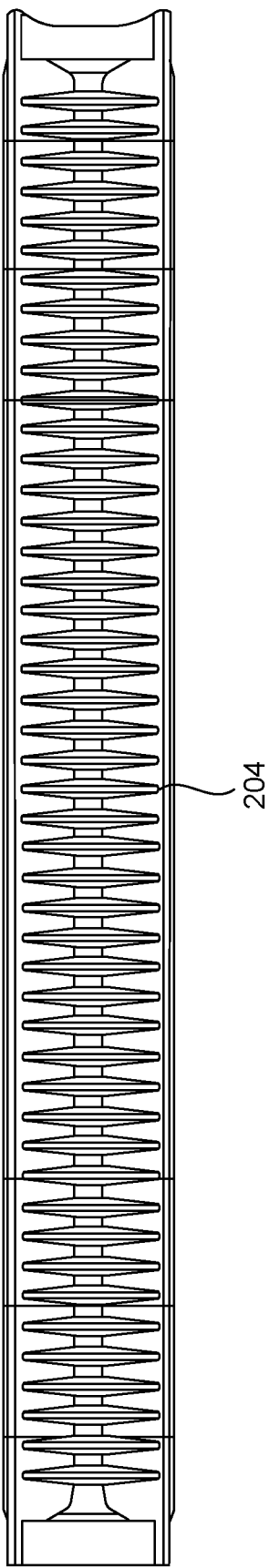
FIGS. 8-9 illustrate an inflatable member according to an embodiment.
Figure 9:
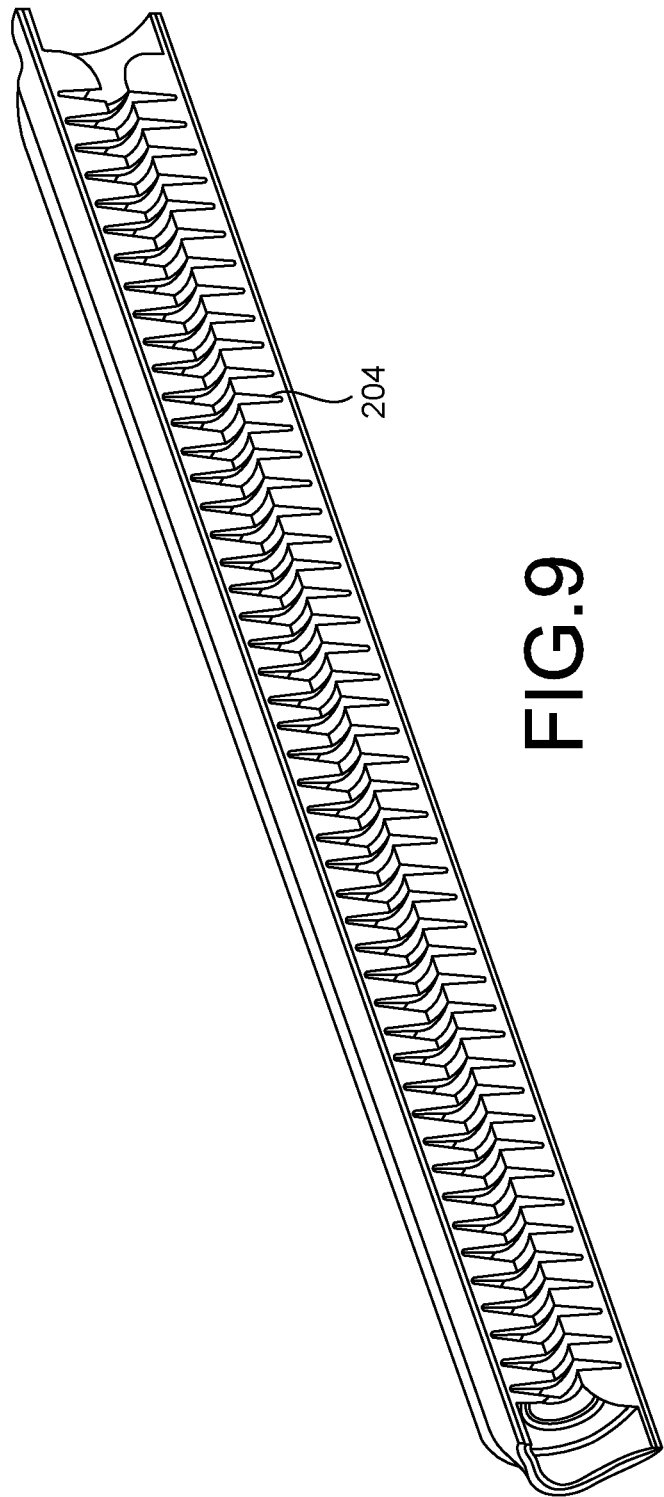

FIGS. 8 and 9 illustrate a cross-sectional side view and a cross-sectional perspective view, respectively. In some embodiments, the inflatable member 204 extends in length and/or the size of the outside diameter of the inflatable member 204 increases when an amount of pressure is placed or applied to the lumen of the inflatable member 204. In some embodiments, when a pressure is placed or applied to the lumen of the inflatable member, the pressure is evenly applied to all portions of the lumen of the inflatable member. In other embodiments, when a pressure is placed or applied to the lumen of the inflatable member, the pressure is applied to different portions of the lumen in different amounts.

In one embodiment, when pressure was applied to the lumen of the inflatable member at 20 pounds per square inch, the overall length of the inflatable member increased by about 0.01 inch and the outside diameter of the inflatable member increased by about 0.026 inches. In another embodiment, when pressure was applied to the lumen of the inflatable member at 20 pounds per square inch, the overall length of the inflatable member increased by about 0.014 inches and the outside diameter of the inflatable member increased by about 0.016 inches. In other embodiments, the length and diameters changed at different amounts.

In one embodiment, when pressure was applied to the lumen of the inflatable member at 10 pounds per square inch, the overall length of the inflatable member increased by about 0.005 inches and the outside diameter of the inflatable member increased by about 0.012 inches. In another embodiment, when pressure was applied to the lumen of the inflatable member at 10 pounds per square inch, the overall length of the inflatable member increased by about 0.007 inches and the outside diameter of the inflatable member increased by about 0.008 inches. In other embodiments, the length and diameters changed at different amounts.

In one embodiment, when pressure was applied to the lumen of the inflatable member at 5 pounds per square inch, the overall length of the inflatable member increased by about 0.002 inches and the outside diameter of the inflatable member increased by about 0.003 inches. In another embodiment, when pressure was applied to the lumen of the inflatable member at 5 pounds per square inch, the overall length of the inflatable member increased by about 0.004 inches and the outside diameter of the inflatable member increased by about 0.005 inches. In other embodiments, the length and diameters changed at different amounts.

The pump assembly 201 may switch between an inflation mode in which the fluid in the reservoir 202 is transferred to the inflatable member 204 (or inflatable members) through the pump assembly 201 in a first direction (e.g., inflation direction) and a deflation mode in which the fluid in the inflatable member 204 (or inflatable members) is transferred back to the reservoir 202 through the pump assembly 201 in a second direction (e.g., deflation direction).

An end cap 290 may be coupled to the end portions of the sidewall 280. In some embodiments, an end cap 290 is coupled to each of the end portions of the sidewall 280. In some embodiments, the end caps 290 help facilitate the fluidic sealing of the lumen 282. The end caps 290 may be coupled to the end portions of the sidewall via an adhesive or any other know coupling method. In some embodiments, the end cap may be shaped as the ends, tips or caps 224 or 232.

The pump assembly 201 includes a pump bulb member or pump 231, a valve body 233, and a selection member 239. The selection member may be used to select or change the mode in which the pump assembly 201 is in. For example, the selection member 239 may be moved from a first position to a second position to place the device in its deflation mode. The selection member 239 may then be moved back to its first position to place the device in its inflation mode. In some embodiments, the selection member 239 is movable with respect to the valve body 233. For example, the selection member 239 may be slidably coupled or slideable with respect to the valve body 233. In some embodiments, the selection member 239 includes stop members, such as shoulders or detents that engage members of the valve body 233 to lock or help retain the selection member 239 in one of its first and second positions. In other embodiments, the selection member 239 may be disposed or coupled to another portion of the device.

The pump 231 may be squeezed or depressed by the user in order to facilitate the transfer of fluid from the reservoir 202 to the inflatable member 204. For example, in the inflation mode, while the user is operating the pump 231, the pump 231 may receive the fluid from the reservoir 202, and then output the fluid to the inflatable member 204. When the user switches to the deflation mode, at least some of the fluid can automatically be transferred back to the reservoir 202 (due to the difference in pressure from the inflatable member 204 to the reservoir 202). Then, the user may squeeze the inflatable member 204 to facilitate the further transfer of fluid through the pump 231 to the reservoir 202.

Then, when the user wants to deflate the inflatable members 204, the user moves selection member 239 to its deflate position. The user may then operate the pump 231 to deflate the inflatable members 204 (i.e., move the fluid from the inflatable members 204 to the reservoir 202). For example, the user may repeatedly depress or squeeze the pump 231 until the deflation is completed. The pump 231 may then return to its original form, which provides a suction force causing fluid to be drawn into the pump 231 from the inflation members 204. The fluid from the inflation members 204 fills the pump 231 (or at least partially fills the pump 231). This pump cycle is repeated until the inflatable members 204 are deflated.

In some examples, the fluid may automatically (upon movement of the selection member 239 to its deflate position) flow out of the inflatable member 204 and into the reservoir 202 without the user depressing or squeezing the pump 231 until the pressure is at least partially equalized between the reservoir 202 and the inflatable member 204.

In some examples, after the inflation member 204 has been deflated, the pump 231 may be squeezed to place the pump in a contracted position or configuration.

Figure 14A:
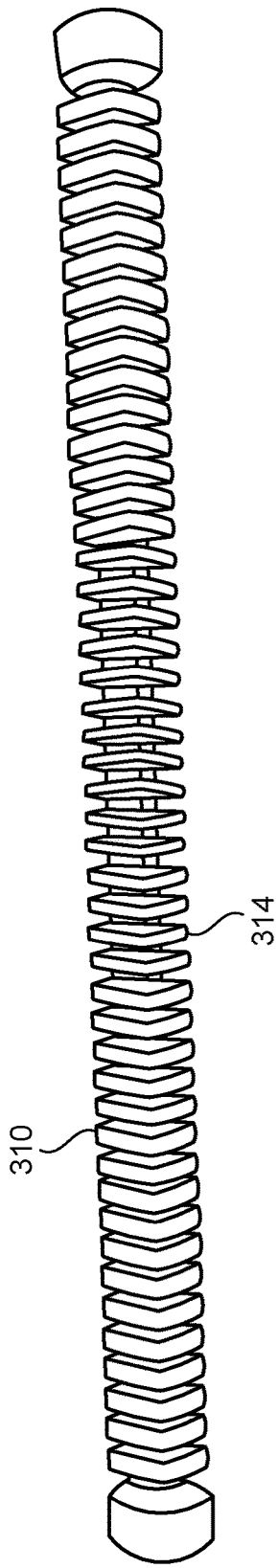
FIG. 14A is a side view of a core member according to an embodiment.
Figure 14B:
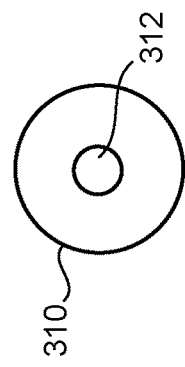
FIG. 14B is an end view of the core member of FIG. 14A.

FIGS. 14A, 14B, and 15-18 illustrate a process for manufacturing an inflatable member according to an embodiment. FIGS. 14A and 14B illustrate a core member 310. The core member 310 is formed to have an outer surface 314 having a shape of the desired inner surface of the inflatable member. The core member 310 is formed of a material that may be melted or dissolved. For example, in some embodiments, the core member 310 is formed of a wax material. In the illustrated embodiment, the core member 310 defines a lumen 312. The lumen 312 of the core member 310 may help facilitate the dissolving or melting of the core member 310, as will be discussed in more detail below.

Figure 15:
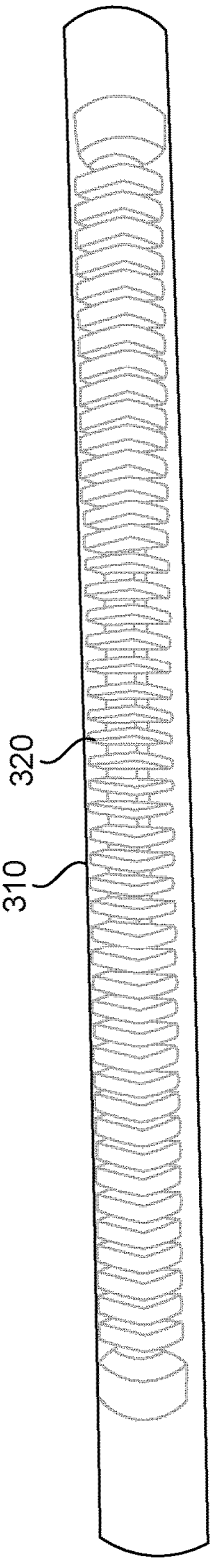
FIGS. 15-18 illustrate an inflatable member being formed according to an embodiment.

As illustrated in FIG. 15, the core member 310 is disposed or placed within a lumen of a tubular member 320. In some embodiments, the tubular member 320 is an extruded tubular member 320. In some embodiments, the tubular member 320 is made of silicone. In other embodiments, it may be formed of anther material such as a material that may help limit the expansion of the inflation member once formed.

Figure 16:
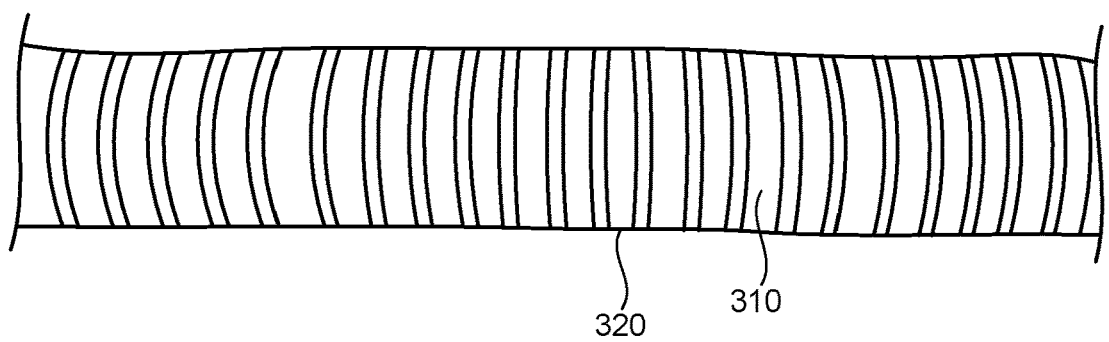
Figure 17:
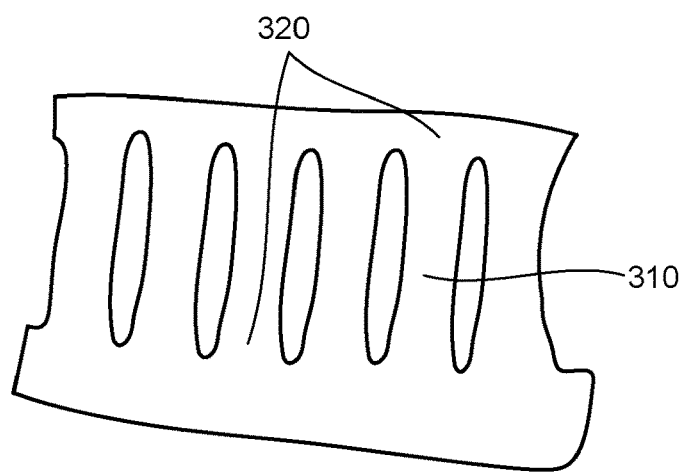

As illustrated in FIGS. 16 and 17, material is then injected between the core member 310 and the tubular member 320. The injected material flows around the core member 310 and adheres to the tubular member 320. In some embodiments, the material that is injected is a silicone material. For example, the material that is injected may be platinum cure silicone. In other embodiments, it is a different type of material is injected.

Figure 18:
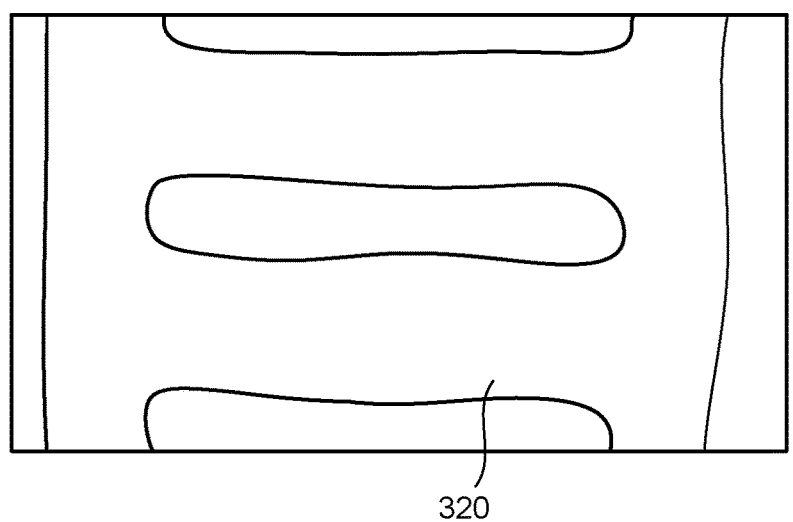

As illustrated in FIG. 18, the core member 310 is then removed. In some embodiments, the core member 310 is melted or dissolved to remove the material of the core member 310. In some embodiments, the core member 310 is heated. In some embodiments, a fluid is passed through the lumen 312 of the core member 310 to facilitate the melting or dissolving of the material of the core member 310.

Figure 19:
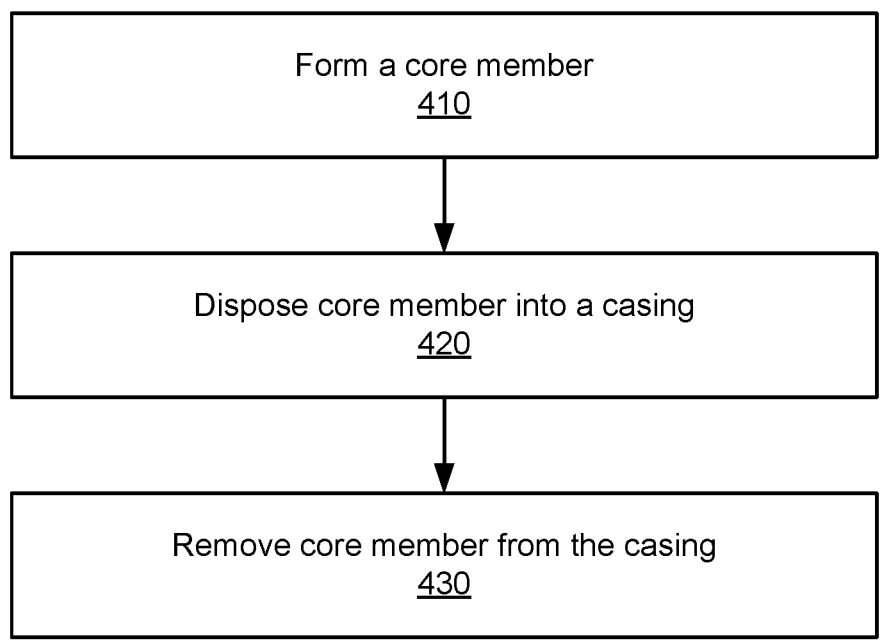
FIG. 19 is a flow chart of a method of making an inflatable member of a penile prosthesis according to an embodiment.

FIG. 19 is a flow chart for a method 400 of forming an inflatable member. At 410, the core member is formed. At 420, the core member is disposed within a lumen of a casing or tubular member. At 430, the core member is removed from the tubular member or casing. In some embodiments, the material of the core member is melted or dissolved and removed from the tubular member or the casing.

Figure 5A:
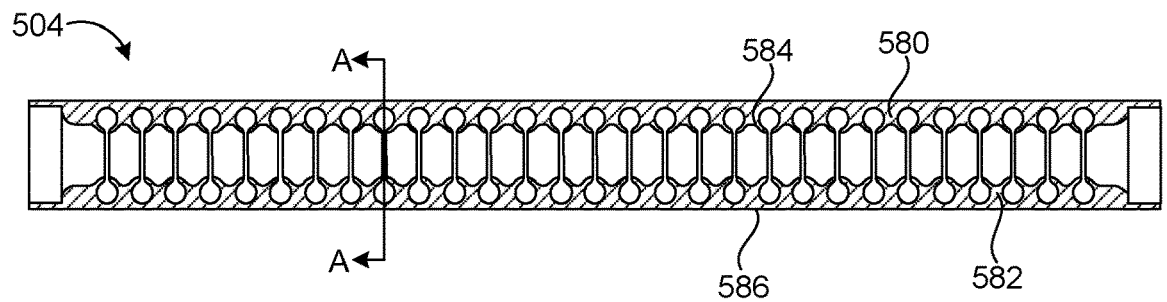
FIGS. 5A, 5B, and 5C are cross-sectional views of an inflatable member according to an embodiment.
Figure 5B:
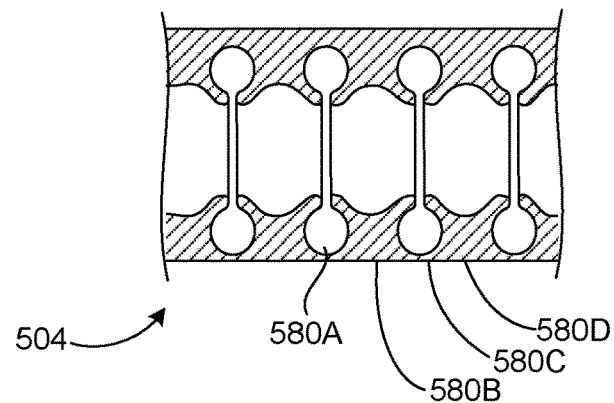
Figure 5C:
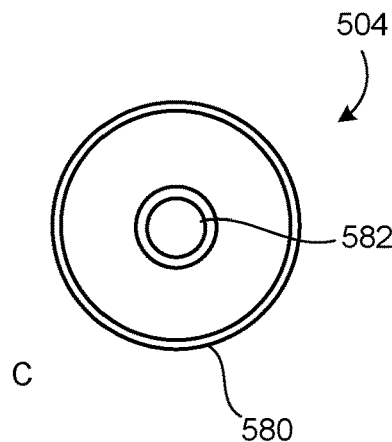

FIGS. 5A, 5B, and 5C illustrate an inflatable member 504 according to another embodiment. FIG. 5A is a cross-sectional view of the inflatable member 504 taken along the longitudinal axis of the inflatable member 504. FIG. 5B is a cross-sectional view of a portion of the inflatable member 504. FIG. 5C is a cross-sectional view of the inflatable member 504 taken along line B-B of FIG. 5A. The inflatable member 504 may be capable of expanding upon the injection of fluid into a cavity of the inflatable member 504. For instance, upon injection of the fluid into the inflatable member 504, the inflatable member 504 may increase its length and/or width, as well as increase its rigidity.

In the illustrated embodiment, the inflatable member 504 includes a sidewall 580 that defines a lumen or cavity 582. In the illustrated embodiment, the inflatable member 504 includes structural features. In some embodiments, the structural features may allow the inflatable member to be inflated at a relatively low pressure. In some embodiments, this may allow the user to inflate the inflatable member 504 with less pumps or activations of the pump or may allow the user to apply less force to the pump to inflate the inflatable member 504. Additionally, in some embodiments, the structural features of the inflatable member 504 may allow the inflatable member 504 to retain or maintain a tubular shape (or a more anatomically correct shape) when the inflatable member 504 is in its deflated configuration.

In the illustrated embodiment, the structural features of the inflatable member 504 include a sidewall 580 that includes structural features. The sidewall 580 has an inner surface 584 and an outer surface 586. The outer surface 586 is disposed opposite the inner surface 584. The inner surface 584 defines the cavity or lumen 582 (and is disposed adjacent the lumen 582). The inner surface 584 of the sidewall 580 has a series of undulations. In other words, the inner surface 584 of the sidewall 580 is not smooth. The series of undulations extend along the longitudinal axis of the inflatable member 504.

In the illustrated embodiment, the sidewall 580 includes portions of increased thickness and portions of decreased thickness. For example, at location 580A the sidewall 580 has a smaller or decreased thickness. At location 580B, the sidewall 580 has a larger or increased thickness. The thickness of the sidewall 580 at location 580A is smaller than at location 580B. The sidewall 580 has a smaller or decreased thickness at location 580C. The sidewall 580 has a larger or increased thickness at location 580D. Locations 580A, 580B, 580C, and 580D are disposed along the longitudinal axis of the inflatable member 504 with location 580B being disposed between 580A and 580C and location 580C being disposed between 580B and 580D.

In the illustrated embodiment, the size or diameter of the lumen 582 defined by the sidewall 580 varies along the longitudinal axis of the inflatable member. Specifically, as illustrated, the portion of the lumen disposed adjacent location 580A of the sidewall 580 is larger than the portion of the lumen disposed adjacent location 580B of the sidewall 580. Similarly, the portion of the lumen disposed adjacent location 580C of the sidewall 580 is larger than the portion of the lumen disposed adjacent location 580D of the sidewall 580.

Figure 6A:
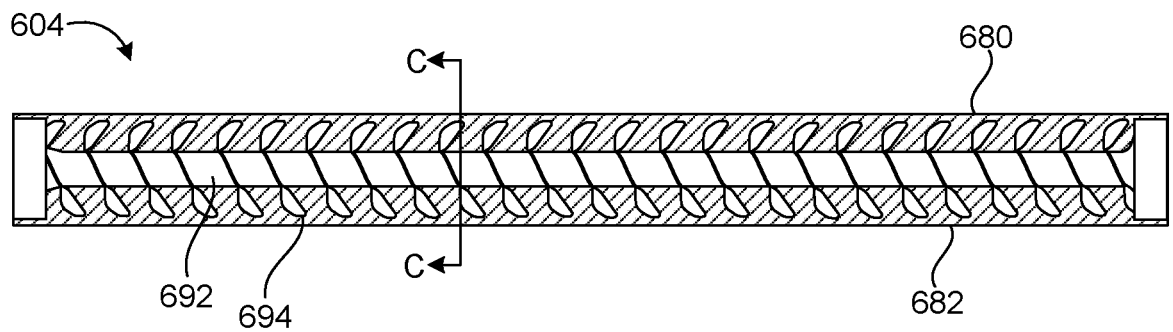
FIGS. 6A, 6B, and 6C are cross-sectional views of an inflatable member according to an embodiment.
Figure 6B:
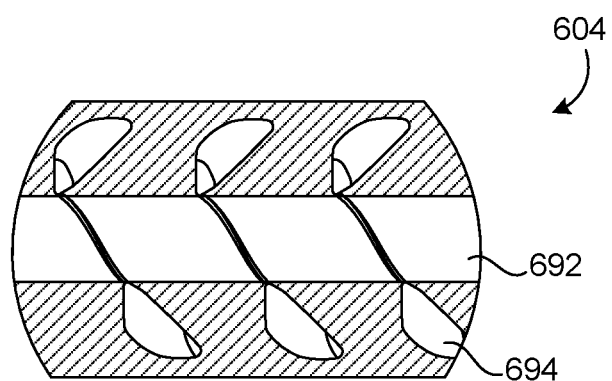
Figure 6C:
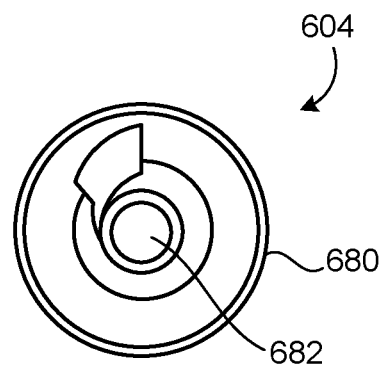

FIGS. 6A, 6B, and 6C illustrate an inflatable member 604 according to another embodiment. FIG. 6A is a cross-sectional view of the inflatable member 604 taken along the longitudinal axis of the inflatable member 604. FIG. 6B is a cross-sectional view of a portion of the inflatable member 604. FIG. 6C is a cross-sectional view of the inflatable member 604 taken along line C-C of FIG. 6A. The inflatable member 604 may be capable of expanding upon the injection of fluid into a cavity of the inflatable member 604. For instance, upon injection of the fluid into the inflatable member 604, the inflatable member 604 may increase its length and/or width, as well as increase its rigidity.

In the illustrated embodiment, the inflatable member 604 includes a sidewall 680 that defines a lumen or cavity 682. The lumen 682 includes a first portion 692 and a second portion 694. The first portion 692 of the lumen 682 extends from one end of the inflatable member 604 to another end of the inflatable member 604 and is substantially linear (extends along or parallel to the longitudinal axis of the inflatable member 604). The second portion 694 of the lumen 682 forms a spiral or helix that extends along the length of the inflatable member 604.

In the illustrated embodiment, the structural features that form the portions of the lumen may allow the inflatable member to be inflated at a relatively low pressure. In some embodiments, this may allow the user to inflate the inflatable member 604 with less pumps or activations of the pump or may allow the user to apply less force to the pump to inflate the inflatable member 604. Additionally, in some embodiments, the structural features of the inflatable member 604 may allow the inflatable member 604 to retain or maintain a tubular shape (or a more anatomically correct shape) when the inflatable member 704 is in its deflated configuration.

Figure 7A:
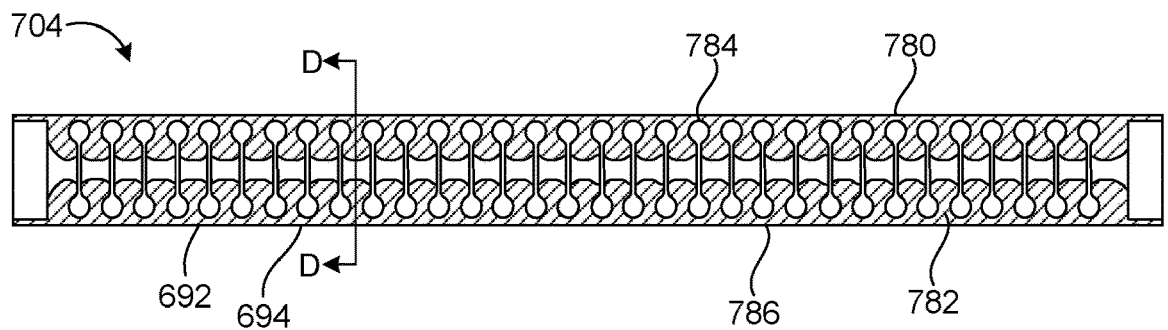
FIGS. 7A, 7B, and 7C are cross-sectional views of an inflatable member according to an embodiment.
Figure 7B:
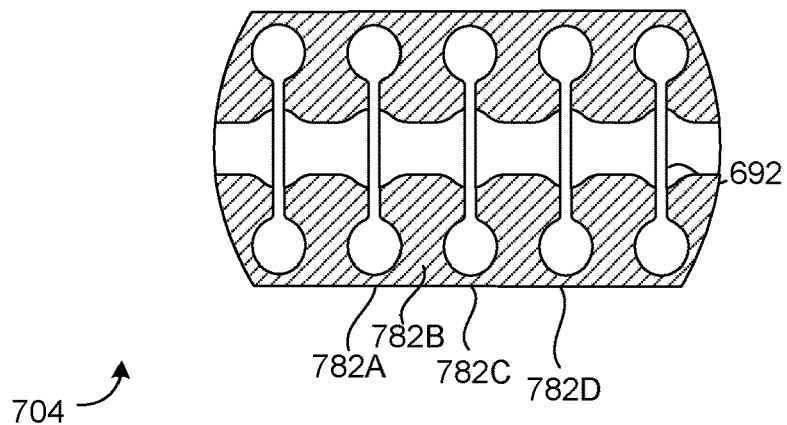
Figure 7C:
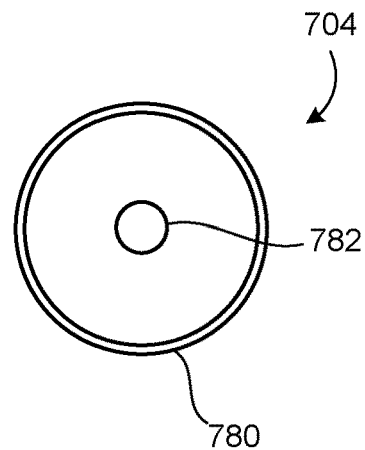

FIGS. 7A, 7B, and 7C illustrate an inflatable member 704 according to another embodiment. FIG. 7A is a cross-sectional view of the inflatable member 704 taken along the longitudinal axis of the inflatable member 704. FIG. 7B is a cross-sectional view of a portion of the inflatable member 704. FIG. 7C is a cross-sectional view of the inflatable member 704 taken along line D-D of FIG. 7A. The inflatable member 704 may be capable of expanding upon the injection of fluid into a cavity of the inflatable member 704. For instance, upon injection of the fluid into the inflatable member 704, the inflatable member 704 may increase its length and/or width, as well as increase its rigidity.

In the illustrated embodiment, the inflatable member 704 includes a sidewall 780 that defines a lumen or cavity 782. In the illustrated embodiment, the inflatable member 704 includes structural features. In some embodiments, the structural features may allow the inflatable member to be inflated at a relatively low pressure. In some embodiments, this may allow the user to inflate the inflatable member 704 with less pumps or activations of the pump or may allow the user to apply less force to the pump to inflate the inflatable member 704. Additionally, in some embodiments, the structural features of the inflatable member 704 may allow the inflatable member 704 to retain or maintain a tubular shape (or a more anatomically correct shape) when the inflatable member 704 is in its deflated configuration.

In the illustrated embodiment, the structural features of the inflatable member 704 include a sidewall 780 that includes structural features. The sidewall 780 has an inner surface 784 and an outer surface 786. The outer surface 786 is disposed opposite the inner surface 784. The inner surface 784 defines the cavity or lumen 782 (and is disposed adjacent the lumen 782). The inner surface 784 of the sidewall 780 has a series of undulations. In other words, the inner surface 784 of the sidewall 780 is not smooth. The series of undulations extend along the longitudinal axis of the inflatable member 704.

In the illustrated embodiment, the sidewall 780 includes portions of increased thickness and portions of decreased thickness. For example, at location 780A the sidewall 780 has a smaller or decreased thickness. At location 780B, the sidewall 780 has a larger or increased thickness. The thickness of the sidewall 780 at location 780A is smaller than at location 780B. The sidewall 780 has a smaller or decreased thickness at location 780C. The sidewall 780 has a larger or increased thickness at location 780D. Locations 780A, 780B, 780C, and 780D are disposed along the longitudinal axis of the inflatable member 704 with location 780B being disposed between 780A and 780C and location 780C being disposed between 780B and 780D.

In the illustrated embodiment, the size or diameter of the lumen 782 defined by the sidewall 780 varies along the longitudinal axis of the inflatable member. Specifically, as illustrated, the portion of the lumen disposed adjacent location 780A of the sidewall 780 is larger than the portion of the lumen disposed adjacent location 780B of the sidewall 780. Similarly, the portion of the lumen disposed adjacent location 780C of the sidewall 780 is larger than the portion of the lumen disposed adjacent location 780D of the sidewall 780.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An implant, comprising:
an inflatable member; and
a pump assembly configured to facilitate a transfer of a fluid from a reservoir to the inflatable member,
the inflatable member having a sidewall that defines a lumen, the sidewall having an outer surface and an inner surface disposed opposite the outer surface, the sidewall being formed of a material, the material extending from the inner surface to the outer surface, the inner surface having a series of undulations such that the lumen defined by the sidewall of the inflatable member includes a first portion having a first diameter, a second portion having a second diameter, and a third portion having a third diameter, the second portion being disposed between the first portion and the third portion along a longitudinal axis of the inflatable member, the second diameter begin larger than the first diameter, the second diameter being larger than the third diameter, the sidewall having the first portion having a first thickness and the second portion having a second thickness, the second thickness being smaller than the first thickness.

2. The implant of claim 1, wherein the outer surface of the inflatable member is substantially smooth.

3. The implant of claim 1, wherein the outer surface of the inflatable member includes a series of undulations.

4. The implant of claim 1, wherein the inflatable member is unitarily formed.

5. The implant of claim 1, wherein the inflatable member is configured to be placed in an inflated configuration and a deflated configuration, the inflatable member having a tubular shape when in the deflated configuration.

6. The implant of claim 1, wherein the inflatable member is configured to be placed in an inflated configuration and a deflated configuration, the inflatable member configured to extend along a longitudinal axis when placed in the inflated configuration.

7. The implant of claim 1, further comprising:
a first cap coupled to a first end portion of the inflatable member; and
a second cap coupled to a second end portion of the inflatable member.

8. The implant of claim 1, further comprising:
a reservoir configured to retain the fluid,
wherein the pump is configured to help facilitate a transfer of the fluid from the reservoir to the inflatable member when the implant is in an inflation mode.

9. The implant of claim 1, wherein the pump assembly includes a valve body and a pump bulb member.

10. A method of making an elongate member of a penile implant, comprising:
forming a core member having a longitudinal axis and an outer surface, the outer surface having a series of undulations;
disposing the core member within a lumen of a casing;
placing material between the core member and the casing before the removing of the core member to form the elongate member such that the inner surface has a series of undulations and a lumen defined by the sidewall of the elongate member includes a first portion having a first diameter, a second portion having a second diameter, and a third portion having a third diameter, the second portion being disposed between the first portion and the third portion along a longitudinal axis of the inflatable member, the second diameter being larger than the first diameter, the second diameter being larger than the third diameter, the first portion of the elongate member has a first thickness and the second portion of the elongate member has a second thickness, the second thickness being smaller than the first thickness; and
removing the core member from the casing.

11. The method of claim 10, wherein the core member is formed of a material that is configured to dissolve.

12. The method of claim 10, wherein the removing the core member from the casing includes dissolving the core member.

13. An implant, comprising:
an inflatable member; and a pump assembly configured to facilitate a transfer of a fluid from a reservoir to the inflatable member, the inflatable member being unitarily formed and having a sidewall that defines a lumen, the sidewall having an outer surface and an inner surface disposed opposite the outer surface, the sidewall being formed of a solid material extending from the inner surface to the outer surface, the inner surface having a series of undulations such that the lumen defined by the sidewall of the inflatable member includes a first portion having a first diameter, a second portion having a second diameter, and a third portion having a third diameter, the second portion being disposed between the first portion and the third portion along a longitudinal axis of the inflatable member, the second diameter begin larger than the first diameter, the second diameter being larger than the third diameter, the outer surface being substantially smooth.

14. The implant of claim 13, wherein the inflatable member is configured to be placed in an inflated configuration and a deflated configuration, the inflatable member having a tubular shape when in the deflated configuration.

15. The implant of claim 13, wherein the inflatable member is configured to be placed in an inflated configuration and a deflated configuration, the inflatable member configured to extend along a longitudinal axis when placed in the inflated configuration.

16. The input of claim 13, further comprising:
a first cap coupled to a first end portion of the inflatable member; and
a second cap coupled to a second end portion of the inflatable member.

17. The implant of claim 13, further comprising:
a reservoir configured to retain the fluid,
wherein the pump is configured to help facilitate a transfer of the fluid from the reservoir to the inflatable member when the implant is in an inflation mode.

18. The implant of claim 13, wherein the pump assembly includes a valve body and a pump bulb member.

19. The implant of claim 1, wherein the first portion extends from a first location along the longitudinal axis to a second location along the longitudinal axis.

20. The implant of claim 13, wherein the first portion extends from a first location along the longitudinal axis to a second location along the longitudinal axis.

* * * * *